United States Patent
Gilbert et al.

(10) Patent No.: US 6,313,149 B1
(45) Date of Patent: Nov. 6, 2001

(54) DIAMINOPYRAZOLES

(75) Inventors: Adam Matthew Gilbert, Congers, NY (US); Zhen-jia Chen, Bothell, WA (US)

(73) Assignee: American Home Products Corporation, Madison, NJ (US)

(*) Notice: Subject to any disclaimer, the term of this patent is extended or adjusted under 35 U.S.C. 154(b) by 0 days.

(21) Appl. No.: 09/655,891

(22) Filed: Sep. 6, 2000

Related U.S. Application Data

(62) Division of application No. 09/327,065, filed on Jun. 7, 1999, now Pat. No. 6,172,222.
(60) Provisional application No. 60/099,348, filed on Jun. 8, 1998.

(51) Int. Cl.[7] .................. A61K 31/415; A61K 31/4155; A61K 31/435; C07D 401/02; C07D 401/06
(52) U.S. Cl. .................. 514/341; 546/268.1; 546/268.4; 546/275.4
(58) Field of Search ..................... 546/138, 139, 546/152, 268.1, 268.4, 275.4; 514/279, 336, 341

(56) References Cited

U.S. PATENT DOCUMENTS 5,008,263    4/1991    Cooper et al. .

OTHER PUBLICATIONS

Primeau et al., Current Pharmaceutical Design, I, 391, 1995.
D. Moderhack, Liebigs Ann., 777–779, 1996.
E. Mohamady et al., J. Heterocyclic Chem. 20, 1501–1503, 1983.
Vincentini et al., Tetrahedron, vol. 46, 5777–5788, 1990.
Vincentini et al., Tetrahedron, Lett., 29, 6171–72, 1988.
CA 132: 176966, Liu Changlin et al., 1998.
CA 131: 129990, Bernard J. Banks, 1999.
CA 132: 194234, O. Fathalia, 1999.
A new route to the synthesis of imidazo pyrazoles Chiara Vincentini et al Tetrahydron Letters 1988.*

* cited by examiner

Primary Examiner—Alan L. Rotman
Assistant Examiner—Rita Desai
(74) Attorney, Agent, or Firm—Rebecca R. Barrett

(57) ABSTRACT

This invention concerns the treatment of smooth muscle spasticity or excess muscle contraction such as urge urinary incontinence with a compound of the formula

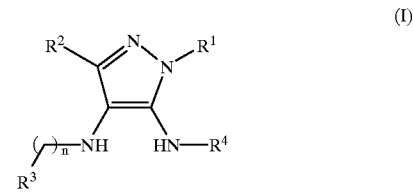

(I)

wherein:
$R^1$ and $R^2$ are independently straight chain alkyl of 1 to 6 carbon atoms, branched alkyl of 3 to 6 carbons atoms, or cycloalkyl of 3 to 6 carbons atoms where $R^1$ $R^2$ may be substituted by F, Cl, Br, I, OH, $NH_2$, cyano, $C_1$–$C_6$ alkoxy, $C_1$–$C_6$alkylthio, COOH or $COOC_1$–$C_6$ alkyl;
$R^3$ is an aryl or heteroaryl as defined herein, optionally substituted with 0 to 4 groups selected independently from $C_1$–$C_6$ alkyl, $C_1$–$C_6$ alkoxy, cyano, F, Cl, Br, $C_1$–$C_6$ alkylthio, $CO_2R^1$, $CONH_2$, OH, $NH_2$, and $NO_2$;
n is 0 or 1;
$R^4$ is a straight chain alkyl group of 1 to 10 carbons atoms, a branched alkyl of 3 to 10 carbons, or a cycloalkyl of 3 to 10 carbons;
and all crystalline forms and the pharmaceutically acceptable salts thereof

4 Claims, No Drawings

DIAMINOPYRAZOLES

This application is a divisional application of U.S. Ser. No. 09/327,065, filed Jun. 7, 1999 now, 6,172,222 which claims benefit of prior U.S. Provisional application No. 60/099,348, filed Jun. 8, 1998.

FIELD OF INVENTION

This invention concerns 4,5-diamino derivatives of (1H)-pyrazoles and their use in the treatment of disorders associated with smooth muscle contraction. Such disorders include, but are not limited to, urinary incontinence, hypertension, asthma, premature labor, irritable bowel syndrome, congestive heart failure, angina, and cerebral vascular disease.

BACKGROUND OF THE INVENTION

Urge urinary incontinence, the abnormal spontaneous contraction of the bladder detrusor muscle leading to a sense of urinary urgency and involuntary urine loss is currently a condition where there exists an unmet medical need (Primeau et al., *Current Pharmaceutical Design*, 1995, 1, 391). The current treatments for this condition are the use of anticholinergics and anticholinergic/antispasmodics which have the limitations of CNS related side effects and low efficacy which leads to poor patient compliance. Hyperpolarization of bladder smooth muscle leading to the relaxation of detrusor muscle contractions may represent a novel therapeutic approach to urge urinary incontinence.

Few examples of simple 4,5-diaminopyrazoles have appeared in the chemical or patent literature. Moderhack describes the synthesis of several 4,5-diaminopyrazoles as intermediates towards the synthesis of 1,2,4-triazoles (*Liebigs Ann.* 1996, 777–9). Lewis et al. describe the synthesis of various 4,5-diaminopyrazoles (*J. Heterocyclic Chem.* 1983, 20, 1501–3).

The synthetic procedure used to make the diamninopyrazoles reported in this invention record is based on the procedure of Vicentini et al. (*Tetrahedron* 1990, 46, 5777–88 and *Tetrahedron Lett.* 1988, 29, 6171–2) which outlines the synthesis of 4-nitroso-5-aminopyrazoles as intermediates in the synthesis of imnidazole[4,5-c]pyrazoles.

SUMMARY OF THE INVENTION

The present invention discloses compounds represented by the formula (I):

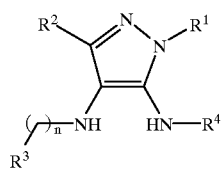

wherein:
$R^1$ and $R^2$ are independently straight chain alkyl of 1 to 6 carbon atoms, branched alkyl of 3 to 6 carbons atoms, or cycloalkyl of 3 to 6 carbons atoms where $R^1 R^2$ may be optionally substituted by F, Cl, Br, I, OH, $NH_2$, cyano, $C_1$–$C_6$ alkoxy, $C_1$–$C_6$ alkylthio, COOH or $COOC_1$–$C_6$ alkyl;
$R^3$ is an aryl or heteroaryl, optionally substituted with 1 to 4 groups selected independently from straight chain $C_1$–$C_6$ alkyl, branched alkyl of 3 to 6 carbons, or a cycloalkyl of 3 to 10 carbons; $C_1$–$C_6$ alkoxy, cyano, F, Cl, Br, $C_1$–$C_6$ alkylthio, $CO_2R^1$, $CONH_2$, OH, $NH_2$, and $NO_2$; wherein aryl is phenyl, naphthalene, anthracene or phenanthrene and heteroaryl is furan, thiophene, pyrrole, irnidazole, oxazole, thiazole, isoxazole, pyrazole, isothiazole, oxadiazole, triazole, thiadiazole, quinolizine, quinoline, isoquinoline, cinnoline, phthalazine, quinazoline, quinoxaline, naphthyridine, pterine, pyridine, pyrazine, pyrimidine, pyridazine, pyran and triazine;

n is 0 or 1;

$R^4$ is a straight chain alkyl group of 1 to 10 carbons atoms, a branched alkyl of 3 to 10 carbons, a cycloalkyl of 3 to 10 carbons, all of which may be optionally substituted by one or more F or Cl atoms; and all crystalline forms, enantiomers, diastereomers, and the pharmaceutically acceptable salts thereof.

It is understood that the definition of the compounds of formula (I), when $R^1$, $R^2$, $R^3$, or $R^4$, contain asymmetric carbons, encompass all possible stereoisomers and mixtures thereof which possess the activity discussed below. In particular, it encompasses racemic modifications and any optical isomers which possess the indicated activity. Optical isomers may be obtained in pure form by standard separation techniques. It is also understood that solid invention compounds or pharmaceutically acceptable salts thereof may exist in more than one crystalline form. The form obtained may be dependent upon the crystallization or recyrstallization solvent or solvent mixture, the rate of heating and/or cooling, drying conditions, and other variables. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Where $R^2$ or $R^3$ contains a carboxyl group, salts of the compounds of this invention may be formed with bases such as alkali metals (Na, K, Li) or the alkaline earth metals (Ca or Mg).

The compounds of formula (I) have been found to relax smooth muscle. They are therefore useful in the treatment of disorders associated with smooth muscle contraction, disorders involving excessive smooth muscle contraction of the urinary tract (such as incontinence), or of the gastro-intestinal tract (such as irritable bowel syndrome), asthma, and hair loss. Furthermore, the compounds of formula (I) relax bladder smooth muscle precontracted with KCl and thus are active as potassium channel activators which render them useful for treatment of peripheral vascular disease, hypertension, congestive heart failure, stroke, anxiety, cerebral anoxia and other neurodegenerative disorders (J. R. Empfield and Keith Russell, "Potassium Channel Openers," Annual Reports in Medicinal Chemistry (1995).

DETAILED DESCRIPTION OF THE INVENTION

The present invention also provides a process for the preparation of a compound of formula (I). More particularly, the compounds of formula (I) where n is 1 may be prepared by reacting a compound of formula (II):

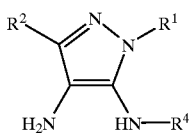

with a compound of formula (III):

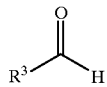

where $R^3$ is an aryl or a heteroaryl moiety optionally substituted with 1 to 4 groups as defined previously, in a solvent such as benzene or toluene in the presence of molecular sieves at room temperature, followed by treatment with hydrogen under a pressure of 1 atmosphere in the presence of Pd/BaSO$_4$ at room temperature, in a polar solvent such as ethyl acetate.

Reaction of compound of formula (II) with a compound of formula (IV):

where $R^3$ is an aryl or heteroaryl moiety as defined previously, in a solvent such as benzene or toluene in the presence of Pd$_2$dba$_3$, P(o-tolyl)$_3$, and NaOt-Bu at 100° C. gives a formula (I) compound where n is 0. The compounds of formula II are prepared by procedures based on the procedure reported by Vicentini et al., *Tetrahedron* 1990, 46, 5777–5788 and *Tetrahedron Lett.* 1988, 29, 6171–6172 as given in steps 1–4 in Example 1.

The following examples are included for illustrative purposes only and are not to be construed as limiting to this disclosure in any way. The chemicals and intermediates are either commercially available or readily prepared according to standard literature procedures. Still other methods of preparation of invention compounds may be apparent to those skilled in the art of organic synthesis.

EXAMPLE 1

N(3)-(2,2-Dimethyl-propyl)-2,5-dimethyl-N(4)-pyridin-4-ylmethyl-2H-pyrazole-3,4-diamine Step 1

N-(2,5-Dimethyl-2H-pyrazol-3-yl)-2,2-dimethyl-propionamide

To 15.0 g (131 mmol) N-(2,5-Dimethyl-2H-pyrazol-3-yl)-amine in 150 mL pyridine at 0° C. was added 19.3 mL (18.9 g, 158 mmol) of pivaloyl chloride. After stirring at 23° C. for 3.5 hours, the reaction solvent was evaporated, and the residue was evaporated with 2×200 mL toluene. The remaining solid was dissolved in 500 mL EtOAc/200 mL H$_2$O and extracted. The aqueous layer was extracted with 2×100 mL EtOAc, and the combined organics were washed with 1×200 mL brine, dried over MgSO$_4$, filtered and evaporated to an orange solid. Recrystallization from hot hexanes/EtOAc gave 24.45 g (125 mmol, a 96% yield) of the title compound as an off-white, crystalline solid: mp: 86–88° C.; $^1$H NMR (300 MHz, CDCl$_3$): δ1.32 (s, 9H), 2.22 (s, 3H), 3.63 (s, 3H), 5.98 (s, 1H), 7.12 (brs, 1H); IR (KBr, cm$^{-1}$): 3316s, 3274s, 2967m, 2935m, 1673s, 1655m, 1570s, 1514m, 1492m, 1457m; MS (ES) m/z (relative intensity): (196, M$^+$, 100).

Anal. Calcd. for C$_{10}$H$_{17}$N$_3$O: C, 61.51; H, 8.77; N, 21.52. Found: C, 61.33; H, 8.80; N, 21.23.

Step 2

(2,2-Dimethyl-propyl)-(2,5-dimethyl-2H-pyrazol-3-yl)-amine

To 4.7 g (123 mmol) of LiAlH$_4$ in 150 mL of THF at 0° C. was added a solution of 12.0 g (61.45 mmol) of N-(2,5-dimethyl-2H-pyrazol-3-yl)-2,2-dimethyl-propionamide and 100 mL THF in drops over 60 min. After addition is complete, the reaction mixture was heated to 67° C. for 42 h. After cooling to 23° C., 5 mL H$_2$O was carefully added, followed by 5 mL 5N NaOH and 5 mL H$_2$O. The resulting mixture was filtered through Celite, evaporated to a yellow oil, dissolved in 300 mL EtOAc, washed with 1×100 mL brine, 1×100 mL H$_2$O, 1×100 mL brine, dried over MgSO$_4$, filtered and evaporated to give 9.45 g (52.1 mmol, an 85% yield) of the title compound as a light yellow oil. $^1$H NMR (300 MHz, CDCl$_3$): δ0.98 (s, 9H), 2.17 (s, 3H), 2.81 (m, 2H), 3.56 (s, 3H), 5.24 (s, 1H); IR (KBr, cm–$^1$): 3261m, 2956m, 2866m, 1568s, 1476m, 1367m, 1362m, 1267m, 1200m, 729m; MS (ES) m/z (relative intensity): 182 (M$^+$+H, 100).

Anal. Calcd. for C$_{10}$H$_{19}$N$_3$: C, 66.26; H, 10.56; N, 23.18. Found: C, 64.75; H, 10.23; N, 24.67.

Step 3

(2,5-Dimethyl-4-nitroso-2H-pyrazol-3-yl)-(2,2-dimethyl-propyl)-amine

To a 0° C. solution of 8.43 g (46.5 mmol) of (2,2-dimethyl-propyl)-(2,5-dimethyl-2H-pyrazol-3-yl)-amine and 150 mL EtOH was added 20 mL of 10–20% EtONO/EtOH. After stirring at 23° C. for 17 h, and 21 h, 20 mL portions of 10–20% EtONO/EtOH were added. After a total of 42 h, the reaction mixture was evaporated to a purple oil. Flash chromatography on silica gel, eluting with CH$_2$Cl$_2$/EtOAc (8/1 to 4/1 to 2/1), gave a purple solid. Recrystallization from hot hexanes/EtOAc gave 4.04 g (19.2 mmol, a 41% yield) of the title compound as a violet crystalline solid. mp: 83–84° C.; $^1$H NMR (300 MHz, CDCl$_3$): δ1.02 (s, 9H), 2.61 (s, 3H), 3.24 (d, J=6.0 Hz, 2H), 3.76 (s, 3H), 10.23 (brs, 1H); IR (KBr, cm$^{-1}$): 3428w, 3058w, 2963m, 2872w, 1633s, 1550m, 1479w, 1428w, 1222brm, 1134m, 971m; MS (ES) m/z (relative intensity): 211 (M$^+$+H, 100).

Anal. Calcd. for C$_{10}$H$_{18}$N$_4$O: C, 57.12; H, 8.63; N, 26.64. Found: C, 57.18; H, 8.83; N, 26.69.

Step 4

N(3)-(2,2-Dimethyl-propyl)-2,5-dimethyl-2H-pyrazole-3,4-diamine (2,5-Dimethyl-4-nitroso-2H-pyrazol-3-yl)-(2,2-dimethyl-propyl)-amine (3.44 g, 16.36 mmol), 400 mg of 10% Pd/C and 60 mL EtOAc were placed under a balloon of H$_2$ and stirred at 23° C. After 4 h, the reaction mixture was filtered through Celite and evaporated to an orange oil. Flash chromatography on silica gel, eluting with CHCl$_3$/MeOH (20/1), gave a yellow solid. Recrystallization from hot hexanes/EtOAc gave 2.86 g (14.57 mmol, an 89% yield) of the title compound as an off-white crystalline solid. mp: 65–69° C.; $^1$H NMR (300 MHz, CDCl$_3$): δ1.00 (s, 9H), 1.65 (brs, 2H), 2.13 (s, 3H), 2.77 (brs, 2H), 2.89 (brs, 1H), 3.62 (s, 3H); IR (KBr, cm$^{-1}$): 3347–3204brs, 2952s, 2903w, 1599m, 1528m, 1495m, 1477m, 1378m, 1316m; MS (ES) m/z (relative intensity): 197 (M$^+$+H, 100).

Anal. Calcd. for C$_{10}$H$_{20}$N$_4$: C, 61.19; H, 10.27; N, 28.54.
Found: C, 56.19; H, 10.56; N, 26.37

Step 5

N(3)-(2,2-Dimethyl-propyl)-2,5-dimethyl-N(4)-pyridin-4-ylmethyl-2H- pyrazole-3,4-diamine To 400 mg (2.03 mmol) of N(3)-(2,2-Dimethyl-propyl)-2,5-dimethyl-2H-pyrazole-3,4-diamine and 15 mL toluene was added 0.23 mL (261 mg, 2.44 mmol) of 4-pyridinecarboxaldehyde, 500 mg of powdered 4Å molecular sieves and 1 crystal of p-TsOH·H$_2$O. After stirring at room temperature for 14 h, TLC indicated that the starting amine (R$_f$=0.40 (10/1 CHCl$_3$/MeOH)) had been converted to the imine (R$_f$=0.50 (10/1 CHCl$_3$/MeOH). The mixture was filtered through Celite and evaporated to give a yellow oil.

To this oil was added 20 mL EtOAc, 300 mg 5% Pd/BaSO$_4$ and 1 drop of quinoline. This mixture was placed under a balloon of H$_2$, and stirred at room temperature. After 24 h, 200 mg of 5% Pd/BaSO$_4$ was added and the reaction mixture was again stirred under a balloon of H$_2$ at room temperature. After a total of 30 h, TLC indicated that practically all of the starting imine (R$_f$=0.50 (10/1 CHCl$_3$/MeOH) had been converted to the corresponding amine (R$_f$=0.35 (10/1 CHCl$_3$/MeOH). The reaction mixture was filtered through Celite and evaporated to an orange oil. Flash chromatography on silica gel, eluting with CHCl$_3$/MeOH (40/1 to 20/1 to 10/1), gave a yellow solid. Recrystallization from hot hexanes/Et$_2$O gave 315 mg (1.10 mmol, a 54% yield) of the title compound as a yellow crystalline solid. mp: 88–90° C., $^1$H NMR (300 MHz, CDCl$_3$): δ0.94 (s, 9H), 1.70 (brs, 1H), 2.13 (s, 3H), 2.61 (brd, 2H), 2.81–2.90 (brm, 1H), 3.59 (s, 3H), 4.00 (s, 2H), 7.26–7.33 (m, 2H), 8.53–8.60 (m, 2H), IR (KBr, cm$^{-1}$): 3254s, 3047w, 2954m, 2865w, 1604w, 1567m, 1417m, 1389w, MS (ES) m/z (relative intensity): 288 (M$^+$+H, 70).

Anal. Calcd. for C$_{16}$H$_{25}$N$_5$: C, 66.87; H, 8.77; N, 24.37.
Found: C, 66.74; H, 8.73; N, 24.20.

EXAMPLE 2

4-{[5-(2,2-Dimethyl-propylamino)-1,3-dimethyl-1H-pyrazol-4-ylamino]-methyl}-benzonitrile The title compound was prepared according to the procedure for Example 1, Step 5 except that 4-cyanobenzaldehyde was used in place of 4-pyridinecarboxaldehyde and the final product was isolated as the tosylate salt, prepared by stirring the product with 1 equiv. of p-TsOH·H$_2$O in 15 mL Et$_2$O and removing the solvent via rotary evaporation. Off-white solid, yield: 85%, mp: 102–104° C., $^1$H NMR (300 MHz, CDCl$_3$): δ0.78 (s, 9H), 2.00 (s, 3H), 2.20–2.40 (brm, 1H), 3.64 (s, 3H), 4.20–4.50 (brm, 1H), 4.37 (s, 2H), 7.21 (d, J=8.1 Hz, 2H), 7.39 (d, J=8.1 Hz, 2H), 7.50–7.55 (m, 2H), 7.74 (d, J=8.1 Hz 2H), IR (KBr, cm$^{-1}$): 3500–2300brm, 3333m, 2957m, 2865m, 2230m, 1606m, 1592m, 1497w, 1477m, 1216s, 1158s, 1124s, 1032s, 1009s, 819s, 683s, MS (ES) m/z (relative intensity): 312 (M$^+$-p-TsOH+H, 100).

Anal. Calcd. for C$_{25}$H$_{33}$N$_5$O$_3$S: C, 62.09; H, 6.88; N, 14.48.
Found: C, 59.00; H, 6.30; N, 13.18.

EXAMPLE 3

N(3)-(2,2-Dimethyl-propyl)-N(4)-(4-fluoro-benzyl)-2,5-dimethyl-2H-pyrazole-3,4-diamine The title compound was prepared according to the procedure for Example 1, Step 5 except that 4-fluorobenzaldehyde was used in place of 4-pyridinecarboxaldehyde. Yellow solid, yield: 78%, mp: 32–39° C., $^1$H NMR (300 MHz, CDCl$_3$): δ0.93 (s, 9H), 2.11 (s, 3H), 2.55 (s, 2H), 3.59 (s, 3H), 3.93 (s, 2H), 7.01 (m, 2H), 7.27 (m, 2H), IR (KBr, cm$^{-1}$): 3334m, 3272s, 2960m, 2918m, 2869m, 1891w, 1592m, 1508s, 1479s, 1462s, 1364s, 1303s, 1283s, 1224m, 1140m, 993m, 819s, 725s, MS (ES) m/z (relative intensity): 305 (M+H$^+$, 100).

Anal. Calcd. for C$_{17}$H$_{25}$FN$_4$: C, 67.08; H, 8.28; N, 18.40.
Found: C, 66.58; H, 8.54; N, 18.07.

EXAMPLE 4

N(4)-(2,4-Dichloro-benzyl)-N(3)-(2,2-dimethyl-propyl)-2,5-dimethyl-2H-pyrazole-3,4-diamine The title compound was prepared according to the procedure of Example 1, Step 5 except that 2,4-dichlorobenzaldehyde was used in place of 4-pyridinecarboxaldehyde and the final product was isolated as the tosylate salt by dissolving in 20 mL Et$_2$O and stirring with 1 equiv. of p-TsOH·H$_2$O for 1 h, and removing the solvent via rotary evaporation. Off-white solid, yield: 50%, $^1$H NMR (300 MHz, CDCl$_3$): δ0.84 (s, 9H), 1.25 (s, 1H), 2.02 (s, 3H), 2.38 (s, 3H), 2.56 (brs, 1H), 3.71 (s, 3H), 4.26 (s, 2H), 4.29 (s, 2H), 7.10–7.50 (m, 5H), 7.77 (s, J=8.2 Hz, 2H), IR, MS (ES) m/z (relative intensity): 355 (M$^+$-p-TsOH, 100).

Anal. Calcd. for C$_{24}$H$_{32}$Cl$_2$N$_4$O$_3$S: C, 54.65; H, 6.11; N, 10.62.
Found: C, 56.95; H, 6.78; N, 9.02.

EXAMPLE 5

4-{[5-(2,2-Dimethyl-butylamino)-1,3-dimethyl-1H-pyrazol-4-ylamino]-methyl}-benzonitrile Step 1

N-(1,3-Dimethyl-1H-pyrazol-5-yl)-2,2-dimethyl-butyramide

The title compound was prepared according to the procedure of Example 1, Step 1 except that 2,2-dimethylbutyroyl chloride was used in place of pivaloyl chloride. Brown oil, yield: 81%, $^1$H NMR (300 MHz, CDCl$_3$): δ0.91 (t, J=7.4 Hz, 3H), 1.25 (s, 6H), 1.63 (q, J=7.4 Hz, 2H), 2.20 (s, 3H), 3.61 (s, 3H), 7.34 (brs, 1H), IR (KBr, cm$^{-1}$): 3293m, 2968s, 2938s, 2879w, 1667s, 1565s, 1511–1447brs, 1381m, 1285w, 1161w, 774m., MS (ES) m/z (relative intensity): 210 (M$^+$+H, 100).

Anal. Calcd. for C$_{11}$H$_{19}$N$_3$O: C, 63.13; H, 9.15; N, 20.08.
Found: C, 61.83; H, 9.15; N, 18.54.

Step 2

(2,2-Dimethyl-pentyl)-(2,5-dimethyl-2H-pyrazol-3-yl)-amine

The title compound was prepared according to the procedure of Example 1, Step 2. Yellow oil, yield: 91%, $^1$H NMR (300 MHz, CDCl$_3$): δ0.89 (t, 3H), 0.95 (s, 6H), 1.33 (q, 2H), 2.15 (s, 3H), 2.82 (d, 2H), 3.55 (s, 3H), δ5.25 (s, 1H).

Step 3

(2,2-Dimethyl-butyl)-(2,5-dimethyl-4-nitroso-2H-pyrazol-3-yl)-amine

The title compound was prepared according to the procedure of Example 1, step 3. Purple solid, yield: 50%, mp: 45–50° C., $^1$H NMR (300 MHz, CDCl$_3$): δ0.89 (t, 3H), 0.97 (s, 6H), 1.37 (q, 2H), 2.61 (s, 3H), 3.25 (d, 2H), 3.76 (s, 3H), IR (KBr, cm$^{-1}$): 2963s, 2878m, 1632s, 1550s, 1528w, 1477m, 1370m, 1356w, 1285w, 1228m, 1134m, 1080w, 967m, 655w, MS (ES) m/z (relative intensity): 225 (M+H$^+$, 100).

Anal. Calcd. for C$_{11}$H$_{20}$N$_4$O: C, 58.90; H, 8.99; N, 24.98. Found: C, 58.14; H, 8.75; N, 25.56.

Step 4

N(3)-(2,2-Di methyl-pentyl)-2,5-dimethyl-2H-pyrazole-3,4-diamine

The title compound was prepared according to the procedure of Example 1, step 4. Yellow oil, yield: 82%, $^1$H NMR (300 MHz, CDCl$_3$): δ0.89 (t, 3H), 0.95 (s, 6H), 1.33 (q, 2H), 2.15 (s, 3H), 2.78 (s, 2H), 3.65 (s, 3H).

Step 5

4-{[5-(2,2-Dimethyl-butylamino)-1,3-dimethyl-1H-pyrazol-4-ylamino]-methyl}-benzonitrile The title compound was prepared according to the procedure of Example 1, Step 5 except that 4-cyanobenzaldehyde was used in place of 4-pyridinecarboxaldehyde and N(3)-(2,2-dimethyl-pentyl)-2,5-dimethyl-2H-pyrazole-3,4-diamine was used in place of N(3)-(2,2-dimethyl-propyl)-2,5-dimethyl-2H-pyrazole-3,4-diamine. Yellow oil, yield: 19%, $^1$H NMR (300 MHz, CDCl$_3$): δ0.83 (t, 3H), 0.89 (s, 6H), 1.28 (q, 2H), 2.10 (s, 3H), 2.61 (s, 2H), 3.59 (s, 3H), 4.04 (s, 2H), 7.42 (d, 2H), 7.61 (d, 2H), IR (KBr, cm$^{-1}$): 3340m, 2961s, 2877m, 2226s, 1588m, 1565m, 1537m, 1462m, 1378m, 1365m, 1296w, 821w, MS (ES) m/z (relative intensity): 326 (M+H$^+$, 100).

Anal. Calcd. for C$_{19}$H$_{27}$N$_5$: C, 70.12; H, 8.36; N, 21.52. Found: C, 68.87; H, 8.49; N, 20.92.

EXAMPLE 6

N(4)-(2,4-Difluoro-benzyl)-N(3)-(2,2-dimethyl-propyl)-2,5-dimethyl-2H-pyrazole-3,4-diamine The title compound was prepared according to the procedure of Example 1, Step 5 except that 2,4-difluorobenzaldehyde was used in place of 4-pyridinecarboxaldehyde. Yellow gum, yield: 61%, $^1$H NMR (300 MHz, CDCl$_3$): δ0.96 (s, 9H), 2.07 (s, 3H), 2.62 (s, 2H), 3.59 (s, 3H), 3.97 (s, 2H), 6.77–6.86 (m, 2H), 7.13–7.24 (m, 1H), IR (KBr, cm$^{-1}$): 3300 m, 2960m, 2870m, 1588m, 1531m, l500m, 1433m, 1230m, 1176m, 1125m, MS (ES) m/z (relative intensity): 323 (M+H$^+$, +100).

Anal. Calcd. for C$_{17}$H$_{24}$F$_2$N$_4$: C, 63.33; H, 7.50; N, 17.38. Found: C, 62.61; H, 7.59; N, 17.14.

EXAMPLE 7

N(3)-(2,2-Dimethyl-propyl)-2,5-dimethyl-N(4)-pyridin-3-ylmethyl-2H-pyrazole-3,4-diamine The title compound was prepared according to the procedure of Example 1, Step 5 except that 3-pyridinecarboxaldehyde was used in place of 4-pyridinecarboxaldehyde. Yellow gum, yield: 39%, $^1$H NMR (300 MHz, CDCl$_3$): δ0.94 (s, 9H), 2.12 (s, 3H), 2.58 (s, 2H), 3.59 (s, 3H), 4.00 (s, 2H), 7.23(m, 1H), 7.60(m, 1H), 8.55(m, 2H), IR (KBr, cm$^1$): 3289m, 3029w, 2953s, 2867m, 1589m, 1532w, 1478s, 1424m, 1394m, 1296m, 1138m, 1079m, 714m, MS (ES) m/z (relative intensity): 288 (M+H$^+$, 100).

Anal. Calcd. for C$_{16}$H$_{25}$N$_5$: C, 66.87; H, 8.77; N, 24.37. Found: C, 65.20; H, 8.98; N, 23.69.

EXAMPLE 8

N(3)-(2,2-Dimethyl-propyl)-2,5-dimethyl-N(4)-(2,4,6-trimethyl-benzyl)-2H-pyrazole-3,4-diamine The title compound was prepared according to the procedure of Example 1, Step 5 except that 2,4,6-trimethylbenzaldehyde was used in place of 4-pyridinecarboxaldehyde. Tan solid, yield: 47%, mp: 114–120° C., $^1$H NMR (300 MHz, CDCl$_3$): δ0.91 (s, 9H), 2.19 (s, 3H), 2.25 (s, 3H), 2.32 (s, 6H), 2.46 (s, 2H), 3.59 (s, 3H), 3.96 (s, 2H), 6.84(s, 2H), IR (KBr, cm$^{-1}$): 3322 m, 3283s, 2951s, 2922m, 2878m, 2823w, 1583m, 1476s, 1452m, 1285s, 1196m, 851w, 757w, MS (ES) m/z (relative intensity): 329 (M+H$^+$, 100).

Anal. Calcd. for C$_{20}$H$_{32}$N$_4$: C, 73.13; H, 9.82; N, 17.06. Found: C, 73.12; H, 9.97; N, 17.05.

EXAMPLE 9

N(3)-(2,2-Dimethyl-butyl)-2,5-dimethyl-N(4)-pyridin-4-ylmethyl-2H-pyrazole-3,4-diamine The title compound was prepared according to the procedure of Example 5, Step 5 except that 4-pyridinecarboxaldehyde was used in place of 4-cyanobenza ldehyde. Purple oil, yield: 49%, $^1$H NMR (300 MHz, CDCl$_3$): δ0.83 (t, 3H), 0.89 (s, 6H), 1.29 (q, 2H), 2.13 (s, 3H), 2.61 (s, 2H), 2.81(br, 2H), 3.60 (s, 3H), 4.01 (s, 2H), 7.27 (d, 2H), 8.55(d, 2H), IR (KBr, cm$^{-1}$): 3296m, 2970s, 2877m, 1601s, 1462m, 1418m, 1378m, 1296m, 1138w, 993w, 799w, 405w, MS (ES) m/z (relative intensity): 302 (M+H$^+$, 100).

Anal. for C$_{17}$H$_{27}$N$_5$: C, 67.74; H, 9.03; N, 23.23. Found: C, 66.82; H, 9.05; N, 23.53.

EXAMPLE 10

N(4)-Benzyl-N(3)-(2,2-dimethyl-butyl)-2,5-dimethyliNl-2H-pyrazole-3,4-diamine The title compound was prepared according to the procedure of Example 5, Step 5 except that benzaldehyde was used in place of 4icyanobenzaldehyde. Yellow oil, yield: 66%, $^1$H NMR (300 MHz, CDCl$_3$): δ0.82 (t, 3H), 0.87 (s, 6H), 1.27 (q, 2H), 2.12 (s, 3H), 2.59 (s, 2H), 2.61(br, 2H), 3.59 (s, 3H), 3.96 (s, 2H), 7.30 (m, 5H), IR (KBr, cm$^{-1}$): 3297m, 3207w, 2970s, 2877m, 1587m, 1461s, 1377m, 1294m, 1136w, 1081w, 746m, 699s, MS (ES) m/z (relative intensity): 301 (M+H$^+$, 100).

Anal. Calcd. for C$_{18}$H$_{28}$N$_4$: C, 71.96; H, 9.39; N, 18.65. Found: C, 71.02; H, 9.33; N, 17.96.

EXAMPLE 11

N(3)-(2,2-Dimethyl-propyl)-2,5-dimethyl-N(4)-phenyl-2H-pyrazole-3,4-diamine

To 300 mg (2.55 mmol) of N(3)-(2,2-dimethyl-propyl)-2,5-dimethyl-2H-pyrazole-3,4-diamine and 20 mL toluene was added 155 mg (0.51 mmol) P(o-tolyl)$_3$, 343 mg (3.57 mmol) NaOt-Bu, 0.27 mL (400 mg, 2.55 mmol) of bromobenzene and 116 mg (0.128 mmol) of Pd$_2$dba$_3$, and the resulting purple mixture was heated to 100° C. After 5 h, the black reaction mixture was filtered through Celite and the filtrate was poured into 50 mL brine. This aqueous mixture was washed with 3×50 mL EtOAc, and the combined organics were dried over MgSO$_4$, filtered and evaporated to a brown oil. Flash chromatography on silica gel, eluting with CH$_2$Cl$_2$/EtOAc (20/1 to 8/1 to 4/1) gave 402 mg (1.48 mmol, a 58% yield) of the title compound as a light yellow gum. $^1$H NMR (300 MHz, CDCl$_3$): δ0.88 (s, 9H), 2.02 (s, 3H), 2.78 (brs, 2H), 2.90–3.12 (brs, 1H), 3.67 (s, 3H), 4.71 (brm, 1H), 6.55–6.60 (m, 2H), 6.72 (t, J=6.4 Hz, 1H), 7.15 (t, J=7.3 Hz, 2H), IR (KBr, cm$^{-1}$): 3390m, 3262w, 3174w, 3058w, 2955m, 1602s, 1544m, 1516m, 1497s, 1476m, 1394m, 1316s, 991w, 749m, MS (ES) m/z (relative intensity): 273 (M$^+$+H, 100).

Anal. Calcd. for C$_{16}$H$_{24}$N$_4$: C, 70.55; H, 8.88; N, 20.57. Found: C, 70.00; H, 9.20; N, 19.31.

EXAMPLE 12

N(4)-(4-Chloro-2-methyl-phenyl)-N(3)-(2,2-dimethyl-propyl)-2,5-dimethyl-2H-pyrazole-3,4-diamine The title compound was prepared according to the procedure of Example 11 except that bromobenzene was replaced with 2-chloro-5-bromotoluene. Orange gum, yield: 56%, $^1$H NMR (300 MHz, CDCl$_3$): δ0.87 (s, 9H), 1.99 (s, 3H), 2.77 (s, 2H), 3.02 (brs, 1H), 3.67 (s, 3H), 4.52 (s, 1H), 6.32 (d, J=8.4 Hz, 1H), 6.96 (dd, J=2.1, 8.4 Hz, 1H), 7.05 (d, J=2.2 Hz, 1H), IR (KBr, cm$^{-1}$): 3344w, 3282s, 2952s, 2868m, 1580m, 1503s, 1479s, 1460m, 1432m, 1308s, 1137m, 814w, MS (ES) m/z (relative intensity): 321 (M+, 100).

Anal. Calcd. for C$_{17}$H$_{25}$ClN$_4$: C, 63.64; H, 7.85; N, 17.46. Found: C, 63.95; H, 7.81; N, 16.47.

EXAMPLE 13

4-[5-(2,2-Dimethyl-propylamino)-1,3-dimethyl-1H-pyrazol-4-ylamino]-benzonitrile

The title compound was prepared according to the procedure of Example 11 except that bromobenzene was replaced with 4-cyanobenzaldehye. Light-yellow solid, Yield 54%, mp: 131–134, $^1$H NMR (300 MHz, CDCl$_3$): δ0.87 (s, 9H), 2.01 (s, 3H), 2.79 (brs, 2H), 3.02 (brs, 1H), 3.66 (s, 3H), 5.21 (s, 1H), 6.58 (d, J=8.7 Hz, 2H), 7.42 (d, J=8.7 Hz, 2H), IR (KBr, cm$^{-1}$): 3360w, 2961m, 2222m, 1609s, 1515m, 1327w, 1169w, 828w, MS (ES) m/z(relative intensity): 296 (M$^+$–H, 50).

EXAMPLE 14

N(4)-(4-Chloro-phenyl)-N(3)-(2,2-dimethyl-propyl)-2,5-dimethyl-2H-pyrazole-3,4-diamine The title compound was prepared according to the procedure of Example 11 except that bromobenzene was replaced with 4-bromochlorobenzene. Yellow gum, yield: 56%, $^1$H NMR (300 MHz, CDCl$_3$): δ0.88 (s, 9H),1.80–2.15 (brs, 1H), 2.00 (s, 3H), 2.78 (s, 2H), 3.65 (s, 3H), 4.72 (brs, 1H), 6.49 (d, J=8.8 Hz, 2H), 7.09 (d, J=8.8 Hz, 2H), IR (KBr, cm$^{-1}$): 3262m, 3087w, 2955s, 2867m, 1597s, 1491brs, 1394m, 1365m, 1312s, 1253m, 1207w, 1089w, 821m, MS (ES) m/z (relative intensity): 307 (M$^+$+H, 100).

Pharmacology

The smooth muscle relaxing activity of the compounds of this invention was established in accordance with standard pharmaceutically accepted test procedures with representative compounds as follows:

Sprague-Dawley rats (150–200 g) are rendered unconscious by CO$_2$ asphyxiation and then euthanized by cervical dislocation. The bladder is removed into warm (37° C.) physiological salt solution (PSS) of the following composition (mM): NaCl, 118.4; KCl, 4.7; CaCl$_2$, 2.5; MgSO$_4$, 4.7; H$_2$O, 1.2; NaHCO$_3$, 24.9; KH$_2$PO$_4$, 1.2; glucose, 11.1; EDTA, 0.023; gassed with 95% O$_2$; 2/5% CO$_2$; pH 7.4. The bladder is opened and then cut into strips 1–2 mm in width and 7–10 mm in length. The strips are subsequently suspended in a 10 mL tissue bath under an initial resting tension of 1.5 g. The strips are held in place by two surgical clips one of which is attached to a fixed hook while the other is attached to an isometric force transducer. The preparations, which usually exhibit small spontaneous contractions, are allowed to recover for a period of 1 hour prior to a challenge with 0.1 μM carbachol. The carbachol is then washed out and the tissue allowed to relax to its resting level of activity. Following a further 30 min period of recovery an additional 15 mM KCl are introduced into the tissue bath. This increase in KCl concentration results in a large increase in the amplitude of spontaneous contractions (and initiation of contractions in previously quiescent strips) superimposed upon a small increase in basal tone. Following stabilization of this enhanced level of contractile activity, incremental increases in the concentration of test compound or vehicle are introduced into the tissue bath. Contractile activity is measured for each compound or vehicle concentration during the last minute of a 30 minute challenge.

The isometric force developed by the bladder strips is measured using a concentration required to elicit 50% inhibition of pre-drug contractile activity (IC$_{50}$ concentration) and is calculated from this concentration-response curve. The maximum percentage inhibition of contractile activity evoked by a test compound is also recorded for concentrations of test compound less than or equal to 30 μM.

The results of this study are shown in Table I.

TABLE I

Inhibition of Contractions in Isolated Rat Bladder Strips

| Compound | n | IC$_{50}$ (μM) |
|---|---|---|
| Example 1 | 2 | 4.9 |
| Example 2 | 2 | 8.26 |
| Example 3 | 2 | 11.45 |
| Example 4 | 2 | 11.8 |
| Example 5 | 1 | 12.6 |
| Example 6 | 2 | 13.5 |
| Example 7 | 1 | 15.4 |
| Example 8 | 1 | 17.8 |
| Example 9 | 2 | 19.2 |
| Example 10 | 2 | 19.9 |
| Example 11 | 4 | 4.3 |
| Example 12 | 2 | 12.5 |
| Example 13 | 2 | 17.9 |
| Example 14 | 1 | 22.9 |
| Example 15 | 2 | 10.7 |

In addition, we tested the ability of compounds to inhibit the hyperactivity of hypertrophied bladder (detrusor) smooth muscle in conscious female rats with hypertrophied bladders and thereby alleviate urinary incontinence in rats according to the following protocol described by Malmgren et al. (*J. Urol.* 1989, 142, 1134.):

Female Sprague-Dawley rats, ranging in weight from 190–210 g are used. Up to 25 animals are prepared each time. After development of bladder hypertrophy 4–8 animals are used per test.

Compounds are dissolved in PEG-200 and administered by gastric gavage or intravenously in a volume of 5 mL/kg. For primary screening all drugs are administered at the arbitrary dose of 10 mg/kg p.o. to groups of 4 rats.

The animals are anesthetized with halothane. Through a midline incision the bladder and urethra are exposed and a ligature of 4–0 silk is tied around the proximal urethra in the presence of a stainless steel rod (1 mm diameter) to produce a partial occlusion. The rod is then removed. The abdominal region is closed using surgical staples and each rat receives 150,000 units of bicillin C-R. The animals are allowed six weeks to develop sufficient bladder hypertrophy. After six weeks, the ligature is removed under halothane anesthesia and a catheter (PE 60) with a cuff is placed in the dome of the bladder and secured with a purse string suture. The catheter is tunneled under the skin and exteriorized through an opening in the back of the neck. The abdominal incision is sutured and the free end of the catheter sealed. In order to prevent infections the rats receive an injection of bicillin C-R (150000 units/rat). Two days later the animals are used in cystometrical evaluations, The animals are placed in the metabolic cages and the catheter is attached (using a "T" connector) to a Statham pressure transducer (Model P23Db) and to a Harvard infusion pump. A plastic beaker attached to a force displacement transducer (Grass FTO3) is placed under the rat's cage to collect and record urine volume. Animals are allowed 15–30 min to rest before the saline infusion (20 mL/hr for 20 minutes) is started for the first cystometry period. Two hours after the first cystometry period, the rats are dosed with the vehicle or the test compound and one hour later a second cystometry is performed. The following urodynamic variables are recorded:

Basal bladder pressure=the lowest bladder pressure during cystometry

Threshold pressure=bladder pressure immediately prior to micturition

Micturition volume=volume expelled

Micturition pressure=peak pressure during voiding

| | |
|---|---|
| Basal bladder pressure = | the lowest bladder pressure during cystometry |
| Threshold pressure = | bladder pressure immediately prior to micturition |
| Micturition volume = | volume expelled |
| Micturition pressure = | peak pressure during voiding |
| Spontaneous activity = | mean amplitude of bladder pressure fluctuations during filling |

Presentation of Results

The mean value of each variable is calculated before and after compound administration. For each compound the changes in the variables measured are compared to the values obtained before treatment and expressed as percent inhibition. The data are also subjected to 2-way analysis of variance to determine significant (p<0.05) changes in the variable measured.

Criteria for Activity

The most characteristic finding in this rat model is spontaneous bladder contractions which develop during filling. The compounds which inhibit spontaneous contractions by at least 50% at 10 mg/kg p.o. or i.v. (arbitrary chosen dose) are considered active. The results of this study are shown in Table II.

TABLE II

| Inhibition of Spontaneous Contractions In Vivo | | | |
|---|---|---|---|
| Compound | # of animals | dose mg/kg (p.o.) | % Red (F)$^c$ |
| Example 1 | 4 | 10 mg/kg | −36 ± 7 |

$^c$Percent reduction in the total number of spontaneous contractions in the hypertrophied rat bladder model Hence, the compounds of this invention have a pronounced effect on smooth muscle contractility and are useful in the treatment of urinary incontinence, irritable bladder and bowel disease, asthma, hypertension, stroke, and similar diseases as mentioned above, which are amenable to treatment with potassium channel activating compounds by administration, orally parenterally, or by aspiration to a patient in need thereof.

Pharmaceutical Composition

Compounds of this invention may be administered neat or with a pharmaceutical carrier to a patient in need thereof. The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties n suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. For oral administration, either a liquid or solid composition form may be used.

The compositions are preferably adapted for oral administration. However, they may be adapted for other modes of administration, for example, parenteral administration for patient suffering from heart failure.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The present invention further provides a compound of the invention for use as an active therapeutic substance. Compounds of formula (I) are of particular use in the induction of smooth muscle relaxation. The present invention further provides a method of treating smooth muscle disorders in mammals including man, which comprises administering to the afflicted mammal an effective amount of a compound or a pharmaceutical composition of the invention.

We claim:

1. A method of treating disorders associated with spastic or excessive smooth muscle contractions of the urinary tract in a mammal in need thereof which comprises administration to said mammal of a therapeutically effective amount of a compound according to the formula

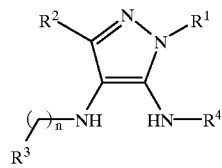

wherein:
$R^1$ and $R^2$ are independently straight chain alkyl of 1 to 6 carbon atoms, branched alkyl of 3 to 6 carbons atoms, or cycloalkyl of 3 to 6 carbons atoms where $R^1$ and $R^2$ may be optionally substituted by F, Cl, Br, I, OH, $NH_2$, cyano, $C_1$–$C_6$ alkoxy, $C_1$–$C_6$ alkylthio, COOH or $COOC_1$–$C_6$ alkyl;

$R^3$ is heteroaryl, optionally substituted with 1 to 4 groups selected independently from straight chain $C_1$–$C_6$ alkyl, branched alkyl of 3 to 6 carbons, or a cycloalkyl of 3 to 10 carbons; $C_1$–$C_6$ alkoxy, cyano, F, Cl, Br, $C_1$–$C_6$ alkylthio, $CO_2R^1$, $CONH_2$, OH, $NH_2$, and $NO_2$; wherein heteroaryl is quinolizine, quinoline, isoquinoline, cinnoline, naphthyridine, and pyridine;

$R^4$ is a straight chain alkyl group of 1 to 10 carbons atoms, a branched alkyl of 3 to 10 carbons, a cycloalkyl of 3 to 10 carbons, all of which may be optionally substituted by one or more F or Cl atoms;

n is 0 or 1;

all crystalline forms;

an enantiomer or diastereomer, or a pharmaceutically acceptable salt thereof.

2. The method according to claim 1 wherein the disorder treated is urge urinary incontinence.

3. A process for the preparation of a compound of Formula I which comprises reacting a compound of formula II

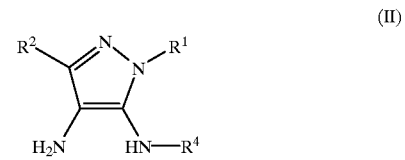

wherein:
$R^1$ and $R^2$ are independently straight chain alkyl of 1 to 6 carbon atoms, branched alkyl of 3 to 6 carbons atoms, or cycloalkyl of 3 to 6 carbons atoms where $R^1$ and $R^2$ may be optionally substituted by F, Cl, Br, I, OH, $NH_2$, cyano, $C_1$–$C_6$ alkoxy, $C_1$–$C_6$alkylthio, COOH or $COOC_1$–$C_6$ alkyl; and $R^4$ is a straight chain alkyl group of 1 to 10 carbons atoms, a branched alkyl of 3 to 10 carbons, a cycloalkyl of 3 to 10 carbons, all of which may be optionally substituted by one or more F or Cl atoms;

with (a) a compound of formula III

wherein:
$R^3$ is heteroaryl, optionally substituted with 1 to 4 groups selected independently from straight chain $C_1$–$C_6$ alkyl, branched alkyl of 3 to 6 carbons, or a cycloalkyl of 3 to 10 carbons; $C_1$–$C_6$ alkoxy, cyano, F, Cl, Br, $C_1$–$C_6$ alkylthio, $CO_2R^1$, $CONH_2$, OH, $NH_2$, and $NO_2$; wherein heteroaryl is quinolizine, quinoline, isoquinoline, cinnoline, naphthyridine, and pyridine, in benzene or toluene as a solvent in the presence of molecular sieves at room temperature, followed by treatment with hydrogen under a pressure of 1 atmosphere in the presence of $Pd/BaSO_4$ at room temperature, in a polar solvent to obtain a formula (I) compound where n is 1,

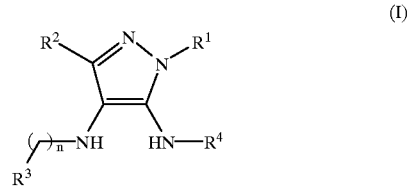

and $R^1$, $R^2$, $R^3$, and $R^4$ are as defined above;

or (b), a compound of the formula

wherein $R^3$ is as defined above;

in benzene or toluene as a solvent in the presence of $Pd_2dba_3$, $P(o\text{-tolyl})_3$, and NaOt-Bu at 100° C. to obtain a formula (1) compound according to the formula

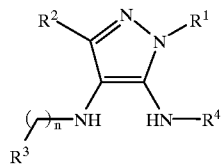
(I)

where n is 0 and

R$^1$ and R$^2$ are independently straight chain alkyl of 1 to 6 carbon atoms, branched alkyl of 3 to 6 carbons atoms, or cycloalkyl of 3 to 6 carbons atoms where R$^1$ and R$^2$ may be optionally substituted by F, Cl, Br, I, OH, NH$_2$, cyano, C$_1$–C$_6$ alkoxy, C$_1$–C$_6$ alkylthio, COOH or COOC$_1$–C$_6$ alkyl;

R$^3$ is heteroaryl, optionally substituted with 1 to 4 groups selected independently from straight chain C$_1$–C$_6$ alkyl, branched alkyl of 3 to 6 carbons, or a cycloalkyl of 3 to 10 carbons; C$_1$–C$_6$ alkoxy, cyano, F, Cl, Br, C$_1$–C$_6$ alkylthio, CO$_2$R$^1$, CONH$_2$, OH, NH$_2$, and NO$_2$; wherein heteroaryl is quinolizine, quinoline, isoquinoline, cinnoline, naphthyridine, and pyridine;

R$^4$ is a straight chain alkyl group of 1 to 10 carbons atoms, a branched alkyl of 3 to 10 carbons, a cycloalkyl of 3 to 10 carbons, all of which may be optionally substituted by one or more F or Cl atoms.

4. The method of claim 1 wherein the mammal is a human.

* * * * *